US006833452B2

(12) United States Patent
Tyagi et al.

(10) Patent No.: US 6,833,452 B2
(45) Date of Patent: Dec. 21, 2004

(54) PROCESS FOR THE PREPARATION OF HIGHLY PURE CRYSTALLINE (R,S)—CEFUROXIME AXETIL

(75) Inventors: Om Dutt Tyagi, Gurgaon (IN); Gyan Chand Yadav, Uttar Pradesh (IN); Vijay Kumar Handa, Chandigarh (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/906,256

(22) Filed: Jul. 16, 2001

(65) Prior Publication Data

US 2002/0016456 A1 Feb. 7, 2002

(30) Foreign Application Priority Data

Jul. 17, 2000  (IN) ..................................... 653/DEL/2000

(51) Int. Cl.[7] ........................................... C07D 501/34
(52) U.S. Cl. ..................................................... 540/222
(58) Field of Search .......................................... 540/222

(56) References Cited

U.S. PATENT DOCUMENTS

| 4,267,320 | A |   | 5/1981  | Gregson et al. |           |
|-----------|---|---|---------|----------------|-----------|
| 4,562,181 | A |   | 12/1985 | Crisp et al.   |           |
| 4,820,833 | A |   | 4/1989  | Crisp et al.   |           |
| 4,994,567 | A |   | 2/1991  | Crisp et al.   |           |
| 5,013,833 | A |   | 5/1991  | Crisp et al.   |           |
| 5,063,224 | A |   | 11/1991 | Mosher et al.  |           |
| 5,677,443 | A | * | 10/1997 | Zenoni et al.  | 540/215   |
| 2003/0171577 | A1 | * | 9/2003 | Kremminger    | 540/225   |
| 2004/0077850 | A1 | * | 4/2004 | Kansal et al. | 540/228   |

FOREIGN PATENT DOCUMENTS

| CN | 1199735 A  | * | 11/1998 |           |
|----|------------|---|---------|-----------|
| EP | 937727     | * | 1/2002  |           |
| GB | 2145409 A  | * | 3/1985  | C07D/501/34 |
| GB | 2145409    |   | 2/1987  |           |
| JP | 05-213968  | * | 11/1993 |           |

OTHER PUBLICATIONS

Abstract for JP02–104590 (Apr. 1990).

* cited by examiner

Primary Examiner—Mark L. Berch
(74) Attorney, Agent, or Firm—Jayadeep R. Deshmukh, Esq.; George E. Heibel, Esq.; William D. Hare, Esq.

(57) ABSTRACT

A process for the preparation of highly pure crystalline form of cefuroxime-1-acetoxyethyl ester (cefuroxime axetil) from cefuroxime by reacting an amine salt of cefuroxime with an esterifying reagent.

21 Claims, No Drawings

PROCESS FOR THE PREPARATION OF HIGHLY PURE CRYSTALLINE (R,S)— CEFUROXIME AXETIL

FIELD OF THE INVENTION

The present invention relates to a process for the preparation of highly pure crystalline form of cefuroxime-1-acetoxyethyl ester (cefuroxime axetil) from cefuroxime in a single step.

BACKGROUND OF THE INVENTION

Cefuroxime is chemically (6R, 7R)-3-carbamoyloxymethyl-7-[(Z)-2-(fur-2-yl)-2-methoxy-iminoacetamido] ceph-3-em-4-carboxylic acid and has the structural Formula II:

FORMULA II

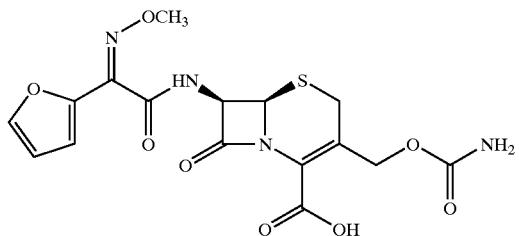

Cefuroxime axetil having the structural Formula I:

FORMULA I

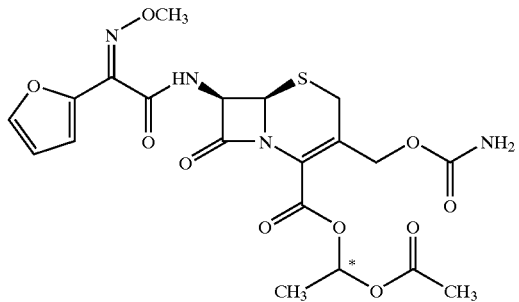

is the 1-acetoxyethyl ester of cefuroxime, a cephalosporin antibiotic with a broad spectrum of activity against gram-positive and gram negative micro-organisms. This compound as well as many other esters of cefuroxime, are disclosed and claimed in U.S. Pat. No. 4,267,320. According to this patent, the presence of an appropriate esterifying group, such as the 1-acetoxyethyl group of cefuroxime axetil, enhances absorption of cefuroxime from the gastrointestinal tract, whereupon the esterifying group is hydrolyzed by enzymes present in the human body. Because of the presence of an asymmetric carbon atom at the 1-position of the 1-acetoxyethyl group, cefuroxime axetil can be produced as R and S diastereoisomers or as a racemic mixture of the R and S diastereoisomers. U.S. Pat. No. 4,267,320 discloses conventional methods for preparing a mixture of the R and S isomers in the crystalline form, as well as for separating the individual R and S diastereoisomers.

The difference in the activity of different polymorphic forms of a given drug has drawn the attention of many workers in recent years to undertake the study on polymorphism. Cefuroxime axetil is the classical example of amorphous form exhibiting higher bioavailability than the crystalline form.

U.S. Pat. No. 4,562,181 and the related U.S. Pat. Nos. 4,820,833; 4,994,567 and 5,013,833, disclose that cefuroxime axetil in amorphous form, essentially free from crystalline material and having a purity of at least 95% aside from residual solvents, has a higher bioavailability than the crystalline form while also having adequate chemical stability. These patents disclose that highly pure cefuroxime axetil can be recovered in substantially amorphous form from a solution containing cefuroxime axetil by spray drying, roller drying, or solvent precipitation. In each case, crystalline cefuroxime axetil is dissolved in an organic solvent and the cefuroxime axetil is recovered from the solution in a highly pure, substantially amorphous form.

Another U.S. Pat. No. 5,063,224 discloses that crystalline R-cefuroxime axetil which is substantially free of S-isomer is readily absorbed from the stomach and gastrointestinal tract of animals and is therefore ideally suited to oral therapy of bacterial infections. According to this patent, such selective administration of R-cefuroxime axetil results in surprisingly greater bioavailability ability of cefuroxime, and thus dramatically reduces the amount of unabsorbable cefuroxime remaining in the gut lumen, thereby diminishing adverse side effects attributable to cefuroxime.

British Patent Specification No. 2,145,409 discloses a process for obtaining pure crystalline cefuroxime axetil and is said to be an improvement over British Patent Specification No. 1,571,683. Sodium cefuroxime is used as the starting material in the disclosed specification, which in turn, is prepared from either 3-hydroxy cefuroxime or cefuroxime. Said process involves an additional step of preparing sodium cefuroxime, and therefore is not economical from commercial point of view.

SUMMARY OF THE INVENTION

It is the object of the present invention to provide an efficient process for the preparation of highly pure crystalline form of cefuroxime axetil. Such a product would not only be useful in being a highly pure form of the active compound but would also be highly useful as a starting material for the preparation of a highly pure, substantially amorphous form of cefuroxime axetil, which has high bioavailability upon oral administration. The present process uses conditions which are convenient to perform on a commercial scale, operationally safe and provides the product in pure form.

Accordingly, the present invention provides a process for the preparation of highly pure crystalline form of cefuroxime axetil of structural Formula I:

FORMULA I

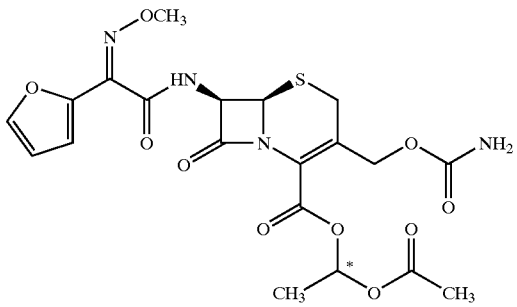

from cefuroxime of structural Formula II:

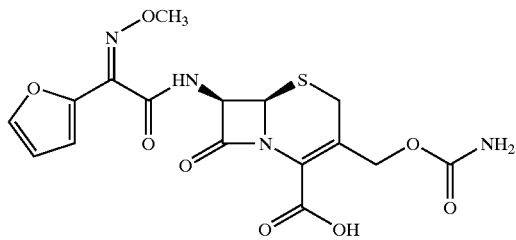

FORMULA II in a single step which comprises preparing an amine salt of cefuroxime followed by its reaction in situ with an esterifying reagent.

Amine salt is prepared by reacting cefuroxime with a suitable amine in the presence of an inert organic solvent, at a temperature from about −15 to about 25° C., the preferred range being −10 to 10° C. and the most preferred range being −10 to 5° C. Cefuroxime axetil is obtained from the amine salt after an esterification reaction and a suitable aqueous work-up. After work-up cefuroxime axetil is thus produced in a single step starting from cefuroxime.

The term "suitable amine" includes primary, secondary, tertiary and cyclic amines. Suitable amine for the preparation of amine salt is selected from ethylamine, diethylamine, diisopropylamine, dibutylamine, di-sec-butylamine, triethylamine, dicyclohexylamine, or didecylamine. Most preferably, dicyclohexylamine is used.

Organic solvent is selected from inert solvents such as N,N-dimethyl-acetamide, N,N-dimethylformamide, N-methylpyrrolidone, acetonitrile, or mixtures thereof. Most preferably, N, N-dimethylacetamide is used.

A preferred reagent for the esterification reaction is (R,S) 1-acetoxy-ethyl bromide and is prepared by the methods known in the literature.

The esterification reaction is generally carried out in the presence of another base. The base required in the esterification step is selected from carbonate or bicarbonate salts of sodium, potassium, calcium or magnesium. Most preferably, potassium carbonate is used.

Suitable aqueous work-up involves the adjustment of pH with mineral acids and extractions with organic solvents. Acids may include hydrochloric acid, sulfuric acid, and phosphoric acid. Hydrochloric acid being the preferred acid. Any organic solvent may be used for extraction and such solvents are known to a person of ordinary skill in the art and include: water-immiscible and partially miscible solvents, such as chloroform, dichloromethane, 1,2-dichloroethane, hexanes, cyclohexane, toluene, methyl acetate, ethyl acetate and the like.

The product may be obtained by reducing the volume of organic solvent containing cefuroxime axetil by evaporation, adding a miscible polar solvent and precipitating the desired product by addition of an anti-solvent or by adding a polar solvent to the solvent system containing cefuroxime axetil and precipitating by addition of anti-solvent. The addition of polar solvent greatly reduces the presence of impurities, specifically $\Delta^2$ isomer of cefuroxime axetil in the final product. Polar solvent may be selected from a group consisting of a lower alkanol, denatured spirit, isopropanol, and the like, ketones such as acetone, or esters such as methyl acetate or ethyl acetate and mixtures thereof. Precipitation may be effected by the addition of appropriate quantities of anti-solvent for the cefuroxime axetil. Suitable anti-solvents include water, alkanes, mixtures of alkanes, such as hexane, cyclohexane or cyclopentane, ethers such as isopropyl ether, or aromatic hydrocarbons, such as benzene or toluene. The polar solvent and an anti-solvent should be at least partially miscible and preferably completely miscible.

Methods known in the art may be used with the process of this invention to enhance any aspect of this process. For example, the solution may be seeded with the crystals of cefuroxime axetil prior to the initiation of product crystallization or the slurry may be cooled prior to filtration. The product obtained may further be purified by recrystallization from solvent(s) using similar conditions for precipitation as those described above which give cefuroxime axetil. This includes dissolving cefuroxime axetil in a solvent and precipitating it with an anti-solvent.

The cefuroxime axetil produced by the process of this invention has an R to S isomer mole ratio of approximately 1:1 and is generally not less than 96% m/m pure, aside from residual solvents and related impurities.

DETAILED DESCRIPTION OF THE INVENTION

Other features of the invention will become apparent in the course of the following description of exemplary embodiment, which is given for illustration of the invention, and are not intended to be limiting thereof.

EXAMPLE 1

Dicyclohexylamine (17.2 g) in N,N-dimethylacetamide (50 ml) was added to a solution of cefuroxime acid (42.4 g) in N,N-dimethylacetamide (300 ml) at about −10° C. (R,S) 1-Acetoxethylbromide (33.4 g) in N,N-dimethylacetamide (50 ml) was added to the above solution and the reaction mixture was stirred for 45 minutes at about −3 to 0° C. Potassium carbonate (1.1 g) was added to the reaction mixture and it was further stirred at that temperature for about 4 hours. The reaction mixture was worked up by pouring into it ethyl acetate (1.0 It), water (1.2 It) and dilute hydrochloric acid (3.5% w/w, 200 ml). The organic layer was separated and the aqueous layer was again extracted with ethyl acetate. The combined organic extracts were washed with water, dilute sodium bicarbonate solution (1%), sodium chloride solution and evaporated in vacuo to give a residue. Methanol was added to the residue and the crude product was precipitated by adding water.

The resulting precipitate was filtered off and recrystallized from the mixture of ethylacetate, methanol and hexane. The precipitated product was filtered, washed and dried to give pure crystalline cefuroxime axetil (42.5 g).

Assay (by HPLC on anhydrous basis)-98.2% w/w; Diastereoisomer ratio-0.53; Total related substances-0.48% w/w.

EXAMPLE 2

Dicyclohexylamine (17.2 g) in N,N-dimethylacetamide (50 ml) was added to a solution of cefuroxime acid (42.4 g) in N,N-dimethylacetamide (300 ml) at about −10° C. (R,S)-1-Acetoxethylbromide (33.4 g) in N,N-dimethylacetamide (50 ml) was added to the above solution and the reaction mixture was stirred for 90 minutes at about −3 to 0° C. Potassium carbonate (1.2 g) was added to the reaction mixture and it was further stirred at that temperature for about 4 hours. The reaction mixture was worked up by pouring into it ethyl acetate (1.0 It), water (1.2 It) and dilute hydrochloric acid (3.5% w/w, 200 ml). The organic layer was separated and the aqueous layer was again extracted with ethyl acetate. The combined organic extracts were washed with water, dilute sodium bicarbonate solution (1%), sodium chloride solution and evaporated in vacuo to give a residue. Methanol was added to the residue and the product was precipitated by adding cyclohexane. The precipitated product was filtered, washed and dried to give pure crystalline cefuroxime axetil (44.5 g).

Assay (by HPLC on anhydrous basis)-99.1% w/w; Diastereoisomer ratio-0.53; Total related substances-0.6% w/w.

While the present invention has been described in terms of its specific embodiments, certain modifications and equivalents will be apparent to those skilled in the art and are intended to be included within the scope of the present invention.

We claim:

1. A process for the preparation of crystalline (R,S)-cefuroxime axetil of Formula I:

FORMULA I

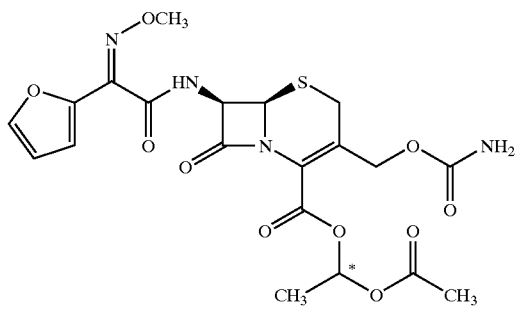

comprising:
a. generating an amine salt of cefuroxime in situ by reacting cefuroxime of Formula II,

FORMULA II

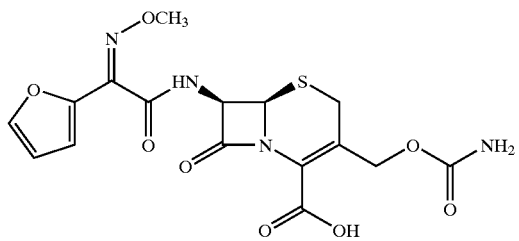

with an amine selected from the group consisting of ethylamine, diethylamine, diisopropylamine, dibutylamine, di-sec-butylamine, triethylamine, dicyclohexylamine, or didecylamine, in an inert organic solvent, b. reacting the amine salt of cefuroxime in situ with (R,S)-1-acetoxyethyl bromide in the presence of a base, and c. followed by aqueous work-up to give crystalline (R,S)-cefuroxime axetil wherein said work-up comprises extracting with an organic solvent followed by the addition of a polar solvent selected from the group consisting of a lower alkanol, ketone, ester and mixtures thereof.

2. The process of claim 1 wherein said amine salt is reacted at a temperature from about −15 to about 25° C.

3. The process of claim 1 wherein the amine is dicyclohexylamine.

4. The process of claim 1 wherein said inert organic solvent is selected from the group consisting of N,N-dimethylacetamide, N,N-dimethylformamide, N-methylpyrrolidone, acetonitrile or mixtures thereof.

5. The process of claim 4 wherein the solvent is N,N-dimethylacetamide.

6. The process of claim 2 wherein temperature range being from about −10 to about 10° C.

7. The process of claim 6 wherein the temperature range being from about −10 to 5° C.

8. The process of claim 1 wherein said base is selected from the group consisting of carbonate or bicarbonate salts of sodium, potassium, calcium or magnesium.

9. The process of claim 8 wherein said base is potassium carbonate.

10. The process of claim 1 wherein said work-up is done in the presence of water and a mineral acid.

11. The process of claim 10 wherein mineral acid is selected from the group consisting of hydrochloric acid, sulfuric acid and phosphoric acid.

12. The process of claim 1 wherein the organic solvent is water-immiscible or partially miscible with water.

13. The process of claim 12 wherein the organic solvent is selected from the group consisting of chloroform, dichloromethane, 1,2-dichloroethane, hexanes, cyclohexane, toluene, methyl acetate and ethyl acetate.

14. The process of claim 1 wherein the polar solvent is selected from the group consisting of methanol, ethanol, denatured spirit, isopropanol, acetone, methyl acetate, ethyl acetate, or mixtures thereof.

15. The process of claim 1 wherein the polar solvent is added after said extraction with an organic solvent and after the amount of organic solvent has been reduced.

16. The process of claim 15 wherein the organic solvent is reduced by evaporation under vacuum.

17. The process of claim 1 further comprising adding an anti-solvent to effect precipitation.

18. The process of claim 17 wherein an anti-solvent is at least partially miscible.

19. The process of claim 18 wherein an anti-solvent is selected from the group consisting of water, alkanes, mixture of alkanes, ethers or aromatic hydrocarbons.

20. The process of claim 19 wherein the anti-solvent is hexane, cyclohexane, cyclopentane, isopropyl ether, benzene or toluene.

21. The process of claim 1 further comprising purifying cefuroxime axetil by recrystallization from solvent(s).

* * * * *